United States Patent [19]

Su

[11] Patent Number: 5,362,914

[45] Date of Patent: Nov. 8, 1994

[54] DECOLORIZATION OF POLYETHYLENE POLYAMINES USING COBALT/COPPER/CHROMIUM

[75] Inventor: Wei-Yang Su, Austin, Tex.

[73] Assignee: Texaco Chemical Inc., White Plains, N.Y.

[21] Appl. No.: 111,580

[22] Filed: Aug. 25, 1993

[51] Int. Cl.$^5$ .......................................... C07C 209/84
[52] U.S. Cl. .................................. 564/498; 564/469; 564/470; 564/478; 564/479; 564/480; 564/497; 564/503; 564/511; 564/512
[58] Field of Search ............... 564/498, 497, 503, 511, 564/512, 478, 479, 480, 469, 470

[56] References Cited

U.S. PATENT DOCUMENTS

| | | | |
|---|---|---|---|
| 3,595,921 | 7/1971 | Pitts | 260/583 |
| 3,723,529 | 3/1973 | Pitts et al. | 260/583 N |
| 4,146,560 | 3/1979 | Larkin et al. | 564/491 |
| 4,570,019 | 2/1986 | Gibson et al. | 564/498 |
| 4,731,165 | 3/1988 | Niebruegge et al. | 203/29 |
| 4,766,247 | 8/1988 | Ford et al. | 564/498 |

FOREIGN PATENT DOCUMENTS 0150075  7/1989  European Pat. Off. .
1351050  4/1974  United Kingdom .

Primary Examiner—Richard L. Raymond
Assistant Examiner—Scott C. Rand
Attorney, Agent, or Firm—James L. Bailey; Kenneth R. Priem; David L. Mossman

[57] ABSTRACT

The present invention relates to a process for the reduction of the color of polyamines by reacting at elevated temperature, e.g. 120°-170° C., and pressure, e.g. 500 to 6000 psig. the colored polyamines, e.g. triethylenetetramine and tetraethylenepentamine, in the presence of a cobalt on alumina hydrogenation catalyst promoted with copper and chromium. In the process of the present invention, the polyamines can either be distilled into a narrow product composition and then hydrogenated, or a crude polyamine product can be hydrogenated and then distilled to produce the desired product composition.

14 Claims, No Drawings

DECOLORIZATION OF POLYETHYLENE POLYAMINES USING COBALT/COPPER/CHROMIUM

FIELD OF THE INVENTION

The invention relates to methods for decolorizing polyamines and more particularly relates, in one embodiment, to methods for decolorizing polyethylene polyamines using catalytic hydrogenation.

BACKGROUND OF THE INVENTION

In the various methods for making polyamines and mixtures thereof, often color bodies are formed which give the polyamine product an undesirable hue. Several processes have been proposed or used commercially for the removal of color bodies from mixed polyamine products. These processes encompass both physical and chemical methods.

For example, U.S. Pat. No. 4,766,247 relates to a process for the reduction of the color of polyamines by reacting at elevated temperature and pressure the colored polyamines, e.g. triethylenetetramine (TETA) or tetraethylenepentamine (TEPA), in the presence of a hydrogenation catalyst, e.g. Raney nickel, palladium or ruthenium on carbon, and a hydrogen atmosphere for a period of time sufficient to effectuate the desired reduction in color. In the '247 process, the polyamines can either be distilled into a narrow product composition and then hydrogenated or a crude polyamine product can be hydrogenated and then distilled to produce the desired product composition.

A process for decolorizing polyethylene polyamines, such as TETA, and higher homologues, such as TEPA, by treatment with active carbon at elevated temperatures followed by distillation is described in U.S. Pat. No. 3,723,529.

U.S. Pat. No. 3,595,921 describes that the color content of the polyethylene polyamine products prepared by the reaction of ethylene dichloride with ammonia is reduced by refluxing the product in the presence of at least about 0.5 wt. % potassium hydroxide for at least one hour at a temperature of about 110° to about 190° C. at the reduced pressure corresponding to the refluxing temperature. Polyethylene polyamine product having a substantially reduced color content is recovered from the refluxing mixture.

A process for decolorizing discolored polyethylene polyamines by distilling the polyamines in the presence of polyethylene polyamine hydrochloride is described in British Patent 1,351,050. Similarly, U.S. Pat. No. 4,570,019 describes a process which may be run continuously for producing polyethylene polyamines having improved color characteristics which comprises treating discolored polyethylene polyamines with polyethylene polyamine hydrochloride in the presence of water at elevated temperatures for the time necessary to reduce the color of the polyethylene polyamines. The decolorized polyethylene polyamines are then flash evaporated from the treating mixture.

A process for decolorizing discolored polyethylene polyamine by contacting the discolored polyamine with a chlorinated hydrocarbon, e.g. an alkyl chloride or an alkylene chloride, and then distilling the resultant mixture to separate the decolored polyamine is mentioned in European Patent 0 150 075 B1.

Finally, U.S. Pat. No. 4,731,165 teaches a process of decoloring crude TETA through contact with a sulfonic acid ion exchange resin. Subsequent distillation at elevated temperature obtains decolored TETA.

Some catalytic hydrogenation decoloration techniques use catalysts with short lifetimes. Others tend to be unduly complicated. Thus, there remains a need for new methods to decolorize polyamines without some of the disadvantages of the prior methods.

SUMMARY OF THE INVENTION

Accordingly, it is an object of the present invention to provide a method for decolorizing polyamines in the presence of hydrogen and a catalyst.

It is another object of the present invention to provide a method for catalytic hydrogenation to decolorize polyethylene polyamines which uses a catalyst having a long life.

In carrying out these and other objects of the invention, there is provided, in one form, a process for reducing the color of a polyamine product comprising contacting the product at elevated temperature and pressure with a catalytically effective amount of a cobalt on alumina hydrogenation catalyst promoted with copper and chromium in the presence of a hydrogen-containing atmosphere.

DETAILED DESCRIPTION OF THE INVENTION

Polyethylene amines such as triethylenetetramine (TETA) and tetraethylenepentamine (TEPA) can be produced by reacting an alkanolamine, an alkyleneamine and optionally either ammonia or a primary or secondary amine in the presence of a catalytic amount of a phosphorous containing catalyst, e.g. phosphoric acid on silica-alumina or Group IIIB metal acid phosphate. The reaction can be conducted at a temperature from about 175° to 400° C., under a pressure sufficient to maintain a substantial amount of ammonia or amine in the reaction zone and particularly under vapor phase conditions. The polyamine product rapidly develops a tan to brown color, i.e. 7–8 on the Gardner color scale, ASTM Method D-1544.

Polyethylene polyamines made by reacting ethylene dichloride and ammonia or reacting an alkyl halide and a diamine also have varied color levels. Indeed, polyethylene polyamines tend to discolor when exposed to air for extended periods, and it is usually recommended that storage vessels be equipped with nitrogen blanketing when the color of the polyamine is important.

Discoloration of the polyamine product produced by any method limits the applications for the discolored TETA and TEPA. The colored products thus have limited commercial potential.

It has been discovered that the color of polyethylene polyamines or other polyalkylene polyamines, and perhaps polyamines in general, may be reduced or eliminated by subjecting them to a mild hydrogenation process. Basically, the polyethylene polyamines made by any process are reacted with a hydrogen atmosphere in the presence of a cobalt hydrogenation catalyst promoted with copper and chromium on an alumina support at elevated temperature and pressure. Without being bound by any particular explanation, it is believed that during the process the chromophores, i.e. color bodies, are reduced or eliminated; the exact mechanism of the process is unknown.

More specifically, the process involves contacting a colored polyamine product with a catalytically effective amount of a Co/Cu/Cr on alumina hydrogenation catalyst in the presence of a hydrogen-containing atmosphere at elevated temperature and pressure. For the process, the polyamine product can be any polyalkylene polyamine. This polyamine product produced by any of the applicable preparation processes can either be treated for color reduction as a crude product, i.e. as produced from the applicable preparation process, or be distilled into selected cuts and then treated. In one embodiment of the invention, the polyamines have at least some compounds with the formula $$NH_2-CH_2CH_2-(NH-CH_2CH_2)_n-NH_2$$

where n ranges from 2 to 6. It will be appreciated that often the polyethylene polyamine will be a mixture of amines. In one embodiment, the greatest single component in the polyamine product is triethylenetetramine; in another, the greatest single component is tetraethylenepentamine.

The catalyst is Co/Cu/Cr on an alumina support. Preferably, the catalyst contains from about 30–40 wt. % cobalt, from about 7–13 wt. % copper, from about 0.1–3 wt. % chromium, with the balance aluminum. The copper and chromium serve as promoters for the cobalt. Enough catalyst should be used to be effective in reducing or eliminating the color in the polyamine product.

The process of the present invention can either be performed in a batch or continuous mode of operation utilizing either a fixed bed or slurry type reactor. Generally, the elevated temperature should be from about 120° to about 170° C., preferably from about 120° to about 160° C. The elevated pressure ranges from about 500 psig to about 6000 psig, preferably from about 1000 to about 5000 psig. If a batch process is used, the batch times may range from about 0.1 to about 4 hours. In a continuous process, the space velocity may range from about 0.1 g/hr-cc catalyst to about 1.0 g/hr-cc catalyst.

The invention will be further illustrated in the following Examples which are not intended to limit the spirit and scope of the invention, but rather merely to more completely illuminate the invention.

Examples 1–3

Color Reduction of TEPA Polyamines

The tests were carried out in a 100 cc electrically heated stainless steel tubular up-flow reactor which was filled with the indicated catalyst (see Table I). TEPA and hydrogen were continuously fed to the heated reactor. Reactor pressure was maintained at 2500 psig with a back pressure regulator. Reactor effluent samples were analyzed by GLC and are given in Table II. Color numbers of reactor effluent samples are listed in Table I.

Example 4

Catalyst Life Study

A catalyst life study on Co/Cu/Cr on alumina for TEPA decolorization was also conducted. The spent catalyst from Example 1 was charged back to the reactor and run at the same conditions for 1000 hours. The reactor effluents were distilled. No significant catalyst activity loss was noted throughout the run..After distillation, TEPA products with colors of Pt-Co 100-125 (green hue) were obtained. The particular catalysts used in these Examples are extrudates, but the catalysts do not have to be limited to those formed by extrusion.

TABLE I

TEPA Decolorization

| Ex. | Catalyst | Temp., °C. | LHSV, g/hr-cc | $H_2$ LHSV (l/hr-cc) | Color (Gardner) Feed | Product |
|---|---|---|---|---|---|---|
| 1 | Co-Cu-Cr/ alumina | 135 | 0.3 | 0.1 | 9 | 2+ |
| 2 | G-62RS (United) | 135 | 0.3 | 0.15 | 9 | 6 |
| 3 | Co-0164 (Engelhard) | 140 | 0.3 | 0.1 | 9 | 5 |

Catalyst G-62RS is 34.5% cobalt on a silica-based support; Co-0164 catalyst is 25% cobalt on a silica-based support.

TABLE II

TEPA Compositions (wt. %)

| Component | Feed | Ex. 1 | Ex. 2 | Ex. 3 |
|---|---|---|---|---|
| Diethylenetriamine (DETA) | 0.251 | 0.376 | 0.629 | 0.541 |
| Triethylenetetramine (TETA) | 1.184 | 1.470 | 1.029 | 1.579 |
| Hydroxyethyl DETA (HEDETA) | 1.509 | 1.333 | 1.002 | 1.457 |
| Piperazinoethylenediamine (PPEDA) | 0.187 | 2.351 | 2.692 | 3.697 |
| Aminoethyl TETA (AETETA) | 10.141 | 9.540 | 9.916 | 9.331 |
| Tetraethylenepentamine (TEPA) | 66.491 | 63.579 | 63.038 | 61.236 |
| Aminoethyl PPEDA (AEPEEDA) | 6.553 | 6.914 | 6.043 | 6.060 |
| Piperazinoethyl DETA (PEDETA) | 8.153 | 8.164 | 7.802 | 8.724 |
| Pentaethylenehexamine (PEHA) | 1.314 | 1.380 | 1.701 | 1.896 |
| Total Others | 4.217 | 4.896 | 6.148 | 5.479 |

Many modifications may be made in the process of this invention without departing from the spirit and scope thereof which are defined only in the appended claims. For example, one skilled in the art may discover that particular reaction conditions, sequences, and Co-Cu-Cralumina catalysts which may not be explicitly recited herein, but which a nevertheless anticipated, would give optimal or otherwise desirable results.

We claim:

1. A continuous process for reducing the color of a polyamine product comprising contacting the product at elevated temperature and pressure with a catalytically effective amount of a cobalt on alumina hydrogenation catalyst promoted with copper and chromium in the presence of a hydrogen-containing atmosphere, where the catalyst has a lifetime in this process of at least 1,000 hours.

2. The process of claim 1 where the elevated temperature is in the range of 120° to 170° C.

3. The process of claim 1 where the elevated pressure is in the range of 500 to 6000 psig.

4. The process of claim 1 where the hydrogenation catalyst contains from about 30–40 wt. % cobalt, about 7–13 wt. % copper, about 0.1–3 wt. % chromium and the balance alumina.

5. The process of claim 1 where the greatest single component in the polyamine product is triethylenetetramine.

6. The process of claim 1 where the greatest single component in the polyamine product is tetraethylenepentamine.

7. The process of claim 1 further comprising distilling the polyamine product following the contacting step to further reduce color.

8. A continuous process for reducing the color of a polyamine product comprising contacting the product at elevated temperature between 120° to 170° C. and pressure between 500 to 6000 psig with a catalytically effective amount of a cobalt on alumina hydrogenation catalyst promoted with copper and chromium in the presence of a hydrogen-containing atmosphere, where the catalyst has a lifetime in this process of at least 1,000 hours.

9. The process of claim 8 where the hydrogenation catalyst contains from about 30–40 wt. % cobalt, about 7–13 wt. % copper, about 0.1–3 wt. % chromium and the balance alumina.

10. The process of claim 8 where the greatest single component in the polyamine product is triethylenetetramine.

11. The process of claim 8 where the greatest single component in the polyamine product is tetraethylenepentamine.

12. The process of claim 8 further comprising distilling the polyamine product following the contacting step to further reduce color.

13. A continuous process for reducing the color of a polyamine product comprising contacting the product at elevated temperature between 120° to 170° C. and pressure between 500 to 6000 psig with a catalytically effective amount of a cobalt on alumina hydrogenation catalyst promoted with copper and chromium containing from about 30–40 wt. % cobalt, about 7–13 wt. % copper, about 0.1–3 wt. % chromium and the balance alumina, in the presence of a hydrogen-containing atmosphere, where the greatest single component in the polyamine product is selected from the group consisting of triethylenetetramine and tetraethylenepentamine, where the catalyst has a lifetime in this process of at least 1,000 hours and where the resulting color of the polyamine product is about Gardner 2.

14. The process of claim 13 further comprising distilling the polyamine product following the contacting step to further reduce color.

* * * * *